United States Patent [19]

Wadden

[11] 4,048,216
[45] Sept. 13, 1977

[54] PROCESS FOR THE MANUFACTURE OF DICYANOBUTENE

[75] Inventor: Dhafir Yusuf Wadden, Wilton, England

[73] Assignee: Imperial Chemical Industries Limited, London, England

[21] Appl. No.: 721,507

[22] Filed: Sept. 8, 1976

[30] Foreign Application Priority Data

Oct. 1, 1975 United Kingdom ............... 40136/75

[51] Int. Cl.$^2$ ........................................... C07C 120/02
[52] U.S. Cl. ................................................ 260/465.3
[58] Field of Search ..................................... 260/465.3

[56] References Cited

U.S. PATENT DOCUMENTS

| 3,347,900 | 10/1967 | Gossel et al. | 260/465.3 |
| 3,470,230 | 9/1969 | Hirsch et al. | 260/465.3 |
| 3,574,701 | 4/1971 | Kominami et al. | 260/465.3 |
| 3,849,472 | 11/1974 | Waddan | 260/465.3 |
| 3,869,501 | 3/1975 | Waddan | 260/465.3 |
| 3,947,487 | 3/1976 | Crooks | 260/465.3 |

FOREIGN PATENT DOCUMENTS 1,084,599 9/1967 United Kingdom

Primary Examiner—Joseph Paul Brust
Attorney, Agent, or Firm—Cushman, Darby & Cushman

[57] ABSTRACT

Butadiene is converted directly to dicyanobutene by reacting with hydrogen cyanide and oxygen or an oxygen-containing gas in the presence of a catalyst comprising copper ions and halide ions and of a solvent for the catalyst.

16 Claims, No Drawings

PROCESS FOR THE MANUFACTURE OF DICYANOBUTENE

This invention relates to organic nitriles, more specifically to dicyanobutene and to a method for its manufacture from butadiene.

It has already been proposed to manufacture dicyanobutene from butadiene by a two-stage process in which butadiene is chlorinated to give dichlorobutene, and the dichlorobutene is then reacted with hydrogen cyanide or an alkali metal cyanide to give dicyanobutene. Apart from the fact that two stages are involved, the method involves the introduction of chlorine and its subsequent removal. It has also been proposed to react butadiene with hydrogen cyanide in presence of a catalyst, for example a zerovalent nickel catalyst, as described, for example, in British Pat. Specification No. 1,104,140, but commercially known methods introduce only one cyano group to give a mixture of pentenenitriles and methylbutenenitriles. The pentenenitriles may subsequently be reacted with further hydrogen cyanide in a separate stage to give adiponitrile, but the latter compound cannot be obtained by this method from butadiene in a single stage in significant yield.

We have now found a method by which two cyano groups may be introduced into the molecule of butadiene in a single stage to give dicyanobutene.

Our invention provides a process for the manufacture of dicyanobutene which comprises reacting butadiene with hydrogen cyanide and oxygen or an oxygen-containing gas in the presence of a catalyst comprising copper ions and halide ions and of a solvent for the catalyst.

The copper ions in the catalyst used in the process of our invention may be added in the cuprous or cupric form. Under the influence of the oxygen used in the process cuprous ions tend to be oxidised to cupric, whereas the hydrocyanation reaction tends to cause the cupric ions to be reduced to cuprous. The copper may be added to the reaction mixture as a halide, for example as cuprous or cupric chloride, bromide or iodide since this will ensure the presence of halide in addition to copper, but this is not essential. Other copper salts may be used, especially the salts of organic acids, more especially the salts of aliphatic carboxylic acids and particularly the salts of alkane carboxylic acids having from 2 to 6 carbon atoms. As examples of such copper salts there may be mentioned copper formate, acetate, propionate, butyrate, lactate, glycollate, acetylacetonate, naphthenate, stearate and benzoate. Moreover, other sources of halide ion may be used for example alkali metal and ammonium chloride, bromide and iodide as well as hydrogen chloride, bromide and iodide and chlorine, bromine and iodine themselves. Further, organic chlorine, bromine and iodine compounds may be used as the halide source, for example tetrabromoethane, chloracetic acid, bromoacetic acid, acetylbromide, dichlorobutene and dibromobutene, as well as hydrochlorides, hydrobromides and hydriodides of organic bases and quaternary ammonium bromides and iodides. It is advantageous also for there to be present an alkali metal salt, for example a sodium, potassium or especially a lithium salt, or an alkaline earth metal salt, for example a beryllium, magnesium, calcium or barium salt. Such a salt is preferably a chloride, bromide or iodide, but may be, for example, an organic acid salt, especially a salt with one of the organic acids specified above as forming suitable copper salts. As examples of such salts there may be mentioned, lithium chloride, lithium bromide, lithium iodide, lithium acetate, lithium propionate, sodium bromide, sodium iodide, sodium acetate, potassium bromide, potassium iodide, potassium acetate and magnesium bromide.

The uptake of oxygen may be assisted by the presence of oxygen carriers, for example, manganese compounds, e.g. manganese gluconate.

As solvents for the catalyst there may be used a wide variety of compounds. The basic requirements are that the catalyst components shall dissolve to a greater or less extent in the solvent and that the solvent shall not interfere with the reaction and shall not itself be extensively changed by the reaction. Thus olefinically unsaturated compounds which react with hydrogen cyanide under the reaction conditions are unsuitable, as are solvents, for example mercaptans, which would be oxidised by the oxygen-containing gas under the reaction conditions. The solvent should preferably be liquid at the reaction temperature and pressure. However, compounds which are normally solid under the reaction conditions may be used dissolved in another solvent.

Water is a suitable solvent as are many organic compounds. Particularly suitable classes of organic compounds include nitriles, alcohols, phenols, ethers, acids, ketones and amides. Suitable nitriles include aliphatic, cycloaliphatic, araliphatic and aromatic nitriles. More especially they include alkyl nitriles and alkylene dinitriles, particularly those having from 1 to 6 carbon atoms in the alkyl or alkylene residue, for example acetonitrile, propionitrile, butyronitrile, hexanonitrile, glutarodinitrile adiponitrile, dicyanobutene and succindinitrile, alkenyl nitriles, for example acrylonitrile, methacrylonitrile, butenenitriles, methyl butenenitriles and pentenenitriles, higher polynitriles, for example tetracyanoethylene, cycloalkyl nitriles, for example cyclohexyl cyanide, aralkyl nitriles, for example benzyl cyanide and $\alpha,\alpha'$-xylylene dinitrile and aryl nitriles, for example benzonitriles, tolunitriles, phthalodinitrile and terephthalodinitrile. Particularly suitable nitriles include acetonitrile, propionitrile and adiponitrile.

Suitable alcohols include aliphatic, cycloaliphatic and araliphatic alcohols. More especially they include alkanols, particularly those having from 1 to 6 carbon atoms, for example methanol, ethanol, n-propanol, isopropanol, butanols, pentanols and hexanols, alkandiols, particularly those having from 1 to 6 carbon atoms, for example ethylene glycol, propane-1,2-diol, propane-1,3-diol, butane-1,4-diol, pentane-diols and hexanediols, alkane-polyols, for example glycerol and trimethylolpropane, aralkanols, for example benzyl alcohol and 2-phenylethanol, and cycloalkanols, for example cyclopentanol, methylcyclopentanols, cyclohexanol and methylcyclohexanols. Particularly suitable alcohols include ethanol and isopropanol.

Suitable phenols include phenol itself, alkylphenols, for example cresols, ethylphenols and xylenols, and halogenophenols, especially chlorophenols and di- and tri-chlorophenols. m-Cresol is a particularly suitable phenol.

Suitable ethers include aliphatic ethers araliphatic ethers, aromatic ethers and cyclic ethers. More especially they include dialkyl ethers, for example di-isopropyl ether and methyl butyl ether, bis-ethers and polyethers for example 1,2-dimethoxyethane, 1,2-dimethyoxypropane and diethyleneglycol dimethyl ether (diglyme), cyclic ethers, for example tetrahydrofuran, tetrahydropyran, dioxan, diphenylene oxide and crown ether (6, 7, 9, 10, 17, 18, 20, 21 - octahydrodibenzo (b, k) (1, 4, 7, 10, 13, 16) - hexaoxacyclooctadecene), alkyl aryl ethers, for example anisole and phenetole, diaralkyl ethers, for example dibenzyl ether, and diaryl ethers for example diphenyl oxide. Dimethyoxyethane, diglyme and tetrahydrofuran are particularly suitable ethers.

Suitable organic acids are especially the carboxylic acids. Suitable carboxylic acids include aliphatic, cycloaliphatic, araliphatic and aromatic carboxylic acids. More especially they include alkane carboxylic acids, particularly those having from 2 to 6 carbon atoms in the alkane residue, for example acetic acid, propionic acid, butyric acid, isobutyric acid, valeric acid or caproic acid, cycloalkane carboxylic acids, for example cyclohexane carboxylic acid and cyclohexylacetic acid, aralkyl caboxylic acids, for example phenylacetic acid, aryl carboxylic acids, for example benzoic acid, toluic acids and anisic acids, and napthenic acids. Acetic acid is particularly suitable.

Suitable ketones include aliphatic, cycloaliphatic, araliphatic, aromatic and cyclic ketones. More especially they include dialkyl ketones, particularly those having from 1 to 6 carbon atoms in the alkyl residues, for example acetone, methyl ethyl ketone and methyl isobutyl ketone, diketones, for example acetylacetone, cyclic ketones, for example cyclopentanone, methylcyclopentanone, cyclohexanone and methylcyclohexanone, alkyl aryl ketones, for example acetophenone, and diaryl ketones, for example benzophenone. Acetone and acetylacetone are particularly suitable ketones.

Suitable amides include in particular aliphatic carboxylic amides and their N-substituted derivatives. More especially they include alkane carboxylic amides, particularly those having from 1 to 4 carbon atoms, and their N-alkyl and N,N-dialkyl derivatives especially those having from 1 to 4 carbon atoms in the alkyl residues, for example formamide, N-methylformamide, N,N-dimethylformamide, acetamide, N,N-dimethylacetamide and propionamide. They also include cyclic amides for example N-methyl-2-pyrrolidone. Dimethylformamide is a particularly suitable amide.

Suitable solvents also include compounds which contain two or more of the functional groups which characterise, respectively, the said nitriles, alcohols, phenols, ethers, acids, ketones and amides, or contain one or more of the said functional groups in combination with some other group. Such compounds include, for example, ether-alcohols, for example ethylene glycol monomethyl and monoethyl ether, nitrile-acids, for example cyanoacetic acid and α-cyanovaleric acid, halogenoacids, for example chloroacetic acid, dichloroacetic acid and trichloroacetic acid, and nitrileesters, for example ethyl cyanoacetate.

Other suitable solvents include esters, especially the esters formed from the alcohols and acids already described as suitable solvents. Particularly suitable esters are the lower alkylesters (e.g. where lower alkyl has from 1 to 4 carbon atoms) of aliphatic mono- or di-carboxylic acids especially those having from 1 to 6 carbon atoms, for example methyl acetate, ethyl acetate, isopropyl acetate, ethyl propionate, methyl butyrate, dimethyl succinate, dimethyl glutarate and diethyl adipate.

Other suitable solvents include hydrocarbons and halogenated hydrocarbons. Such solvents include both aliphatic, cycloaliphatic and aromatic hydrocarbons, and their halogenated derivatives, for example hexane, cyclohexane, benzene, toluene, xylene, chloroform, carbon tetrachloride, trichloroethylene, tetrachloroethane, dibromoethane, chlorobenzene, bromobenzene, dichlorobenzene trichlorobenzene and diphenyl.

Other suitable solvents include thioethers, that is sulphides, including cyclic sulphides, for example dimethyl sulphide, diethyl sulphide, dipropyl sulphide, dibutyl sulphide, diamyl sulphide, dihexyl sulphide, methyl ethyl sulphide, thiophen, tetrahydrothiophen, pentamethylene sulphide, dicyclohexyl sulphide, dibenzyl sulphide, diphenyl sulphide, ditolyl sulphide and thiodiglycol.

Other suitable solvents include sulphoxides and sulphones, especially dialkyl sulphoxides and sulphones, particularly where the alkyl group has from 1 to 6 carbon atoms, and cyclic sulphoxides and sulphones, for example dimethyl sulphoxide, diethyl sulphoxide, diethyl sulphone, dimethyl sulphone, tetramethylene sulphoxide, tetramethylene sulphone (sulpholane) and pentamethylene sulphoxide and pentamethylene sulphone.

The solvents may be used singly or in admixture with each other in any convenient proportions. Moreover the solvents may be used in admixture with other organic compounds which are not in themselves solvents for the catalyst.

The oxygen may be used as such or in admixture with non-reactive gases such as nitrogen. Air is a particularly suitable oxygen-containing gas, but mixtures of oxygen and nitrogen with a higher or lower proportion of oxygen than that of the air may also be used.

The reaction is conveniently carried out at temperatures within the range 10° to 150° C, preferably from 35° to 110° C. The reaction may be carried out at atmospheric pressure or at pressures above or below that of the atmosphere. The process may advantageously be operated under pressure, and pressures may, for example, be from 0.2 up to about 50 bar. Pressures in the range 2 to 10 bar absolute are very suitable.

The reaction may conveniently be carried out by passing butadiene and hydrogen cyanide in vapour form together with oxygen or an oxygen-containing gas through a liquid comprising the catalyst and solvent under the selected temperature and pressure conditions. Alternatively, the butadiene and hydrogen cyanide may be kept in the liquid phase under pressure with the catalyst and solvent, and the oxygen or oxygen-containing gas passed through. It is not essential, however, for the oxygen or oxygen-containing gas to be contacted simultaneously with the catalyst and solvent. It is possible, for example, to pass butadiene and hydrogen cyanide on the one hand and oxygen-containing gas on the other hand alternately through the liquid comprising the catalyst and solvent. Passage of oxygen or oxygen-containing gas in these circumstances leads to a change in the colour of the liquid to dark brown.

The butadiene used in the process of our invention may contain other constituents. For example the butadiene may be admixed with other C$_4$ hydrocarbons, for example butenes and butane. Instead of using butadiene itself, a crude C$_4$ stream from a cracker containing possibly less than 50% of butadiene may be used as the feed in our process to produce dicyanobutene.

Water is formed in the process of our invention, and it may be desirable, for example when using organic solvents, to remove the water from the reaction system. The water is usually taken up into the reactant gas stream and is preferably condensed out from the effluent gas stream at least in part, prior to any recycle.

In carrying out the process of our invention the molar ratio of hydrogen cyanide to butadiene may vary widely, for example over the range 1:10 to 10:1, but preferably over the range 1:2 to 4:1. The oxygen is preferably used in molar excess in relation to whichever of the hydrogen cyanide and butadiene is used in the smaller molar amount.

The catalyst is used in catalytic amount. The amount of copper ion may vary, for example, from 0.001 mole to 0.2 mole per mole of butadiene, although higher proportions are not excluded. The amount of halide ion may vary, for example, within the same molar range, although we prefer that there is at least one mole of halide ion per mole of copper ion. The amount of solvent used may vary widely. There should preferably be at least one mole of solvent per mole of copper ion, and amounts between 5 moles and 100 moles are convenient. When an alkali metal or alkaline earth metal compound is present it may be used in amounts up to several times the molar amount of copper, for example in amounts of from 0.5 to 15 moles per mole of copper.

The dicyanobutene obtained as the product of our process is normally present in the liquid reaction mixture and may be separated therefrom by conventional methods, for example by fractional distillation under reduced pressure, by extraction with solvents, or by a combination of such methods.

The process of our invention is particularly adapted to continuous operation. It may be convenient to take the reaction to only partial completion, to separate at least some of the product and to recycle unchanged material. For this reason times of contact with the catalyst may vary widely. Such times may vary from a few minutes, for example 5 minutes, up to many hours, for example 50 hours.

The dicyanobutene product of our process is principally 1,4-dicyanobutene. This is a valuable intermediate, since it may, by hydrogenation of the double bond, be converted to adiponitrile which itself, on hydrogenation of the nitrile groups, give hexamethylene diamine, an intermediate useful in the manufacture of polymers, for example polyurethanes and especially polyamides, in particular polyamides made by polycondensation with dicarboxylic acids, for example with adipic acid to give polyhexamethylene adipamide (nylon 6.6) useful for the manufacture of mouldings and for melt-spinning into synthetic fibres.

The invention is illustrated but not limited by the following Examples.

EXAMPLE 1

Into a solution of 3g cupric bromide and 0.75g lithium bromide in 30g propionitrile maintained at 50° C there was passed butadiene at a rate of 2.5 l/hour into which had been evaporated liquid hydrogen cyanide at a rate of 4 ml/hour. After 1 hour the passage of the butadiene/hydrogen cyanide mixture was stopped and oxygen was passed through the solution at a rate of 3.5 l/hour for 1 hour when the mixture had become dark brown. The cycle was then repeated. After a total reaction time of 46 hours the reaction mixture was found to contain 2.22g of 1,4-dicyanobutene with no significant amounts of other unsaturated nitriles. The product was isolated by evaporation of the solvent and extraction of the residue with hot toluene.

EXAMPLE 2

Example 1 was repeated except that a solution of 3g of cupric bromide in 30g of propionitrile was used as the catalyst solution. After 46 hours the reaction mixture was found to contain 1.26g of 1,4-dicyanobutene, and after 160 hours 2.56g of 1,4-dicyanobutene.

EXAMPLE 3

Butadiene at a rate of 6,000 parts by volume per hour and oxygen at a rate of 6,000 parts by volume per hour were passed together through liquid hydrogen cyanide, which was thereby evaporated into the gas stream, and the resulting gas stream was passed through a mixture of 20 parts of cupric acetate and 42 parts of lithium bromide in 200 parts by volume of glacial acetic acid held at 90° to 100° C for a period of 9 hours, during which 44 parts by volume of liquid hydrogen cyanide were evaporated into the gas stream. The reaction mixture was diluted with water, extracted with toluene, and the toluene evaporated from the extract. The residue consisted of 9.8 parts, 5% of which was 1,4-dicyanobutene-2 and 91% partly converted material capable of further conversion to dicyanobutene.

EXAMPLE 4

For operation of atmospheric pressure the reactor consisted of a heated, efficiently stirred vessel with a reflux condenser cooled to −6° C. The initial charge contained:

| | |
|---|---|
| propionitrile | 77 parts by weight |
| cupric bromide | 8 parts by weight |
| lithium bromide | 2 parts by weight | and was maintained at 50° C.
The reactants

| | |
|---|---|
| butadiene | 7 parts by wt. per hr. |
| hydrogen cyanide | 6 parts by wt. per hr. |
| oxygen | 8 parts by wt. per hr. | were fed to the reactor. The excess gas can be recovered for recycle.

When steady reaction conditions had been achieved trans-1,4-dicyanobutene-2 was found at a rate of 0.0103 moles per hour per liter of reaction liquid.

EXAMPLE 5

A gas stream consisting of butadiene at a rate of 3 l/hr and oxygen at a rate of 6 l/hr and into which liquid hydrogen cyanide at a rate of 8 ml/hr was fed was passed through a mixture of:

| | |
|---|---|
| Benzonitrile | 100 ml |
| Cupric bromide | 7.9 g |
| Lithium bromide | 2 g | at 50° C stirred at atmospheric pressure for 11 hours. Trans-1,4-dicyanobutene-2 was formed at a rate of 10.7 millimoles per liter of reaction mixture per hour.

I claim:

1. A process for the manufacture of dicyanobutene which comprises reacting butadiene with hydrogen cyanide in the molar ratio of 1:10 to 10:1 and oxygen or an oxygen-containing gas with oxygen in molar excess in relation to whichever of the hydrogen cyanide and butadiene is used in the smaller molar amount, in the presence of a catalyst comprising copper ions and halide ions and of a solvent for the catalyst at a temperature of 10° to 150° C and a pressure of 0.2 to 50 bar, the amount of copper ion and the amount of halide ion being from 0.001 to 0.2 mole per mole of butadiene.

2. The process of claim 1 in which an alkali metal or alkaline earth metal salt is included in the reaction mixture.

3. The process of claim 2 in which the metal salt is a lithium salt.

4. The process of claim 1 in which the solvent is water or an organic solvent.

5. The process of claim 4 in which the organic solvent is a nitrile.

6. The process of claim 4 in which the organic solvent is an acid, an alcohol, a phenol, an ether, a ketone or an amide.

7. The process of claim 5 in which the organic solvent is an alkyl nitrile or alkylene dinitrile having from 1 to 6 carbon atoms in the alkyl or alkylene residue.

8. The process of claim 7 in which the organic solvent in acetonitrile, propionitrile, benzonitrile or adiponitrile.

9. The process of claim 6 in which the organic solvent is acetic acid.

10. The process of claim 1 in which the butadiene is introduced into the reaction mixture as a crude $C_4$ stream containing butadiene.

11. The process of claim 1 in which the reaction is conducted at a temperature of 35° to 110° C.

12. The process of claim 1 in which the reaction is conducted at a pressure of 2 to 10 bar.

13. The process of claim 1 in which the molar ratio of hydrogen cyanide to butadiene is 1:2 to 4:1.

14. The process of claim 1 in which the solvent is present in amounts from 5 to 100 moles per mole of copper ion.

15. The process of claim 2 wherein the alkali metal or alkaline earth metal salt is present in an amount from 0.5 to 15 moles per mole of copper.

16. A process for the manufacture of dicyanobutene which comprises reacting butadiene with hydrogen cyanide in the molar ratio of 1:10 to 10:1 and oxygen or an oxygen-containing gas with oxygen in molar excess in relation to whichever of the hydrogen cyanide and butadiene is used in the smaller molar amount, in the presence of a catalyst consisting essentially of copper ions and an alkali metal or alkaline earth metal salt as a source of halide ions and of a solvent for the catalyst, at a temperature of 10° to 150° C and a pressure of 0.2 to 50 bar, the amount of copper ion and the amount of halide ion being from 0.001 to 0.2 mole per mole of butadiene.

* * * * *

UNITED STATES PATENT OFFICE
CERTIFICATE OF CORRECTION

Patent No. 4,048,216    Dated September 13, 1977

Inventor(s) Dhafir Yusuf Waddan

It is certified that error appears in the above-identified patent and that said Letters Patent are hereby corrected as shown below:

Page 1 of the patent the inventor's last name should read --WADDAN-- (both occurrences).

Signed and Sealed this

Twenty-seventh Day of December 1977

[SEAL]

Attest:

RUTH C. MASON
Attesting Officer

LUTRELLE F. PARKER
Acting Commissioner of Patents and Trademarks